US008691874B2

(12) United States Patent
Karageozian et al.

(10) Patent No.: US 8,691,874 B2
(45) Date of Patent: *Apr. 8, 2014

(54) TREATMENT OF OPHTHALMIC DISORDERS USING UREA

(75) Inventors: Vicken H. Karageozian, Laguna Beach, CA (US); David Castillejos, Irvine, CA (US); John Park, Santa Ana, CA (US)

(73) Assignee: Kato Pharmaceuticals, Inc., Laguna Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/445,822

(22) Filed: Apr. 12, 2012

(65) Prior Publication Data

US 2012/0196937 A1 Aug. 2, 2012

Related U.S. Application Data

(60) Continuation of application No. 11/585,400, filed on Oct. 23, 2006, now abandoned, which is a division of application No. 10/367,614, filed on Feb. 13, 2003, now abandoned, which is a continuation-in-part of application No. 10/215,680, filed on Aug. 9, 2002, now Pat. No. 7,008,960, which is a continuation of application No. 09/517,798, filed on Mar. 2, 2000, now Pat. No. 6,462,071.

(60) Provisional application No. 60/357,347, filed on Feb. 13, 2002, provisional application No. 60/357,574, filed on Feb. 15, 2002.

(51) Int. Cl.
*A61K 31/40* (2006.01)

(52) U.S. Cl.
USPC .......................................... 514/588; 514/912

(58) Field of Classification Search
USPC .................................. 514/588, 912
See application file for complete search history.

(56) References Cited

U.S. PATENT DOCUMENTS

| 4,409,205 A | 10/1983 | Shively |
| 4,820,516 A | 4/1989 | Sawyer et al. |
| 5,110,493 A | 5/1992 | Cherng-Chyi et al. |
| 5,292,509 A | 3/1994 | Hageman |
| 5,441,984 A * | 8/1995 | Heath et al. ........... 514/595 |
| 5,470,881 A | 11/1995 | Charlton et al. |
| 5,474,985 A | 12/1995 | Polansky et al. |
| 5,484,432 A | 1/1996 | Sand |
| 5,554,187 A | 9/1996 | Rizzo, III |
| 5,624,893 A * | 4/1997 | Yanni ..................... 514/2.3 |
| 5,626,865 A | 5/1997 | Harris et al. |
| 5,629,344 A | 5/1997 | Charlton et al. |
| 5,866,120 A | 2/1999 | Karageozian et al. |
| 5,891,084 A | 4/1999 | Lee |
| 5,891,913 A | 4/1999 | Sallmann et al. |
| 6,039,943 A | 3/2000 | Karageozian et al. |
| 6,132,735 A | 10/2000 | Harris et al. |
| 6,156,741 A | 12/2000 | Durrant et al. |
| 6,242,198 B1 | 6/2001 | McBurney |
| 6,242,468 B1 | 6/2001 | Li et al. |
| 6,335,348 B1 | 1/2002 | Ross et al. |
| 6,337,350 B1 | 1/2002 | Rahbar et al. |
| 6,384,056 B1 | 5/2002 | Ross et al. |
| 6,395,758 B1 | 5/2002 | Ross et al. |
| 6,399,648 B1 | 6/2002 | Ross et al. |
| 6,462,071 B1 | 10/2002 | Castillejos |
| 6,506,788 B1 | 1/2003 | Ross et al. |
| 6,551,590 B2 | 4/2003 | Karageozian et al. |
| 7,008,960 B1 | 3/2006 | Castillejos |
| 7,977,385 B2 | 7/2011 | Karageozian et al. |
| 2001/0053347 A1 | 12/2001 | Varani et al. |
| 2003/0199574 A1 | 10/2003 | Karageozian et al. |
| 2005/0137124 A1 | 6/2005 | Castillejos |
| 2007/0105950 A1 | 5/2007 | Karageozian et al. |

FOREIGN PATENT DOCUMENTS

| EP | 0244178 A2 | 11/1987 |
| EP | 0392802 A2 | 10/1990 |
| JP | 1-04023 | 4/1989 |
| WO | WO 94/27591 A1 | 12/1994 |
| WO | WO 00/09105 A2 | 2/2000 |
| WO | WO 00/51620 A1 | 8/2000 |
| WO | WO 00/51620 | 9/2000 |
| WO | WO 01/78702 A2 | 10/2001 |
| WO | WO 01/78703 A2 | 10/2001 |
| WO | WO 03/068166 A2 | 8/2003 |
| WO | WO 03/077898 A1 | 9/2003 |

OTHER PUBLICATIONS

Aaberg, "Macular holes: a review", Surv. Ophthamol., 1970, vol. 15, pp. 139-162.
Allen, J.B., et al., "Nitric Oxide Synthase Inhibitors Exert Differential Time-Dependent Effects on LPS-Induced Uveitis.", Experimental Eye Research, vol. 62, No. 1, Jan. 1996, pp. 21-2, Abstract.
Bishop et al., "Age-Related Changes on the Surface of Vitreous collagen Fibrils", Invest. Ophthalmol. Vis. Sci., 2004, vol. 45, pp. 1041-1046.
Bishop, "Structural Molecules and Supramolecular Organization of the Vitreous Gel", Prog. Retin. Eye Res., 2000, vol. 19, No. 3, pp. 323-344.

(Continued)

*Primary Examiner* — Zohreh Fay
(74) *Attorney, Agent, or Firm* — Knobbe Martens Olson & Bear

(57) ABSTRACT

Methods for treating disorders of the eye and/or disorders of a nerve in a human or veterinary patient by delivering to the patient a therapeutically effective amount of a compound selected from the group of; urea, urea derivatives, thiourea, thiourea derivatives, guanidine, guanidine derivatives and compounds having General Formula I as set forth herein. For ophthalmic applications, the compound may be delivered by intravitreal injection such that the compound causes vitreal liquefaction, posterior vitreoretinal detachment and other affects.

36 Claims, No Drawings

(56) References Cited

OTHER PUBLICATIONS

Bleeker et al., "Urea and the vitreous barrier of the eye", Exp Eye Res 1968;7:30-6.
Brewton et al., "Mammalian Vitreous Humor Contains Networks of Hyaluronan Molecules: Electron Microscopic Analysis using the Hyaluronan-binding region (G1) of Aggrecan and Link Protein", Exp. Cell Res. 198, 1992, pp. 237-249.
Bromberg BB. "Systemic and ocular mechanisms of anuran adaptation to altered environments: effects of electrolyte and urea concentrations in plasma and aqueous humor", Exp Eye Res 1980;30:221-30.
Chen et al., "Results and complications of pneumatic retinopexy", Ophthalmology, 1988, vol. 95, pp. 601-608.
Cordeiro et al., "Effect of Varying the Mitomycin-C Treatment Area in Glaucoma Filtration Surgery in the Rabbit." Invest. Ophthalmol. Vis. Sci., vol. 38 (8), pp. 1639-1646 Jul. 1997.
DiMattio J et al. "Reduced ocular glucose transport and increased non-electrolyte permeability in rats with retinal degeneration (RCS)", Exp Eye Res 1983;37:217-23.
Galin M.A., et al. "A comparison of intraocular pressure reduction following urea and sucrose administration", A.M.A. Archives of Ophthalmology. 1960; 63:281-282.
Galin MA, et al., "Hypotensive effect of urea in inflamed and non inflamed eye" A.M.A Arch Ophthalmol 962;68:633-5.
Hayreh (Exp Review, Opthamol. 2(6), (2007) 889-894.
Hilton et al., "A Two-step Outpatient Operation without Conjunctival Incision", Ophthalmology 1986; 93: 626-641.
International Preliminary Examination Report in PCT/US03/04617 filed on Feb. 13, 2003, date of completion Oct. 10, 2003.
International Search Report in PCT/US00/05587 filed on Mar. 2, 2000, mailed on Jul. 13, 2000.
International Search Report in PCT/US03/04617 filed on Feb. 13, 2003, mailed on Aug. 20, 2003.
International Search Report in PCT/US03/07700 filed on Mar. 14, 2003, mailed on Aug. 15, 2003.
Iwamoto K et al. "Disposition of urea following intravenous administration to rats" Chem Pharm Bull 1982; 30:1422-9.
Kawamura, et al., "Effects of an anti-prostaglandin agent added to the irrigation solution on damage to the anterior segment in monkey eyes induced by pars plana vitrectomy", Nippon Gakkiai Zasshi, Aug. 1989, vol. 93, No. 8, pp. 823-829 (Abstract Only).
Kawashima, S., et al., "Effects of Mitomycin C on the Rat Retna", Database Biosis Online!, Biosciences Information Service, vol. 92, No. 3, 1996, pp. 229-241.
Komichi S. "Studies on the function of iris and ciliary body: report IX on the outflow of urea contained in the anterior chamber", Nippon Ganka Gakkai Zasshi 1964; 68:1089-93.
Komuro S. "Experimental studies on the transport of C14-labeled urea into the aqueous humor of the rabbit eye", Nippon Ganka Gakkai Zasshi 1964;68:1094-1103.
Lane V.M., et al, "Changes in Urea nitrogen and creatine concentrations in the vitreous humor of cattle after death", Am. J. Vet. Res. 1985; 46:1550-1552.
Larsson, "Posterior vitreous detachment. A combined clinical and physicochemical study", Graefe's Arch. Clin. Exp. Ophthalmol, 1985, vol. 223, pp. 92-93.
McCurdy, "Intravenous urea treatment of the painful crisis of Sickle Cell Disease", New England Journal of Medicine, 1971, vol. 285, pp. 992-994.
McDonald et al., "The management of subretinal gas following attempted pneumatic retinal reattachment", Ophthalmology, 1987, vol. 94, pp. 319-326.
McLeod et al., "Trampolines and triangles. The surgical pathology of the vitreous", Trans. Ophthal. Soc. UK, 1997; 97:225-231.
Nickerson et al., "A 'Cleat' Geometry for Suppressing Wall Slip", J. Rheol., 2005, vol. 49, No. 4, pp. 865-874.
Nickerson et al., "Internal Tension: A Novel Hypothesis Concerning the Mechanical Properties of the Vitreous Humor", Macromol. Symp., 2005, vol. 227, pp. 183-189.
Office Action in U.S. Appl. No. 10/389,226 mailed Jun. 19, 2009.
Office Action in U.S. Appl. No. 11/585,400 mailed May 11, 2011.
Office Action in U.S. Appl. No. 11/585,400 mailed Nov. 14, 2011.
Official Action mailed by the Canadian Intellectual Property Office on Feb. 28, 2012 in corresponding Canadian patent application No. 2,475,338 in 2 pages.
Official Action mailed by the Canadian Intellectual Property Office on Aug. 2, 2007 in corresponding Canadian patent application No. 2,366,050 in 3 pages.
Official Action mailed by the Canadian Intellectual Property Office on Sep. 4, 2008 in corresponding Canadian Patent application No. 2,366,050 in 2 pages.
Official Action mailed by the Canadian Intellectual Property Office on Feb. 8, 2010 in corresponding Canadian patent application No. 2,478,965 in 2 pages.
Poliner et al., "New retinal detachment after pneumatic retinopexy", Ophthalmology, vol. 94, pp. 315-318.
Remington, "The Science and Practice of Pharmacy", 1995, 19 Edition, Chapter 62, pp. 1041-1042.
Scott et al., "The Structure of Interfibrillar Proteoglycan Bridges ('Shape Modules') in Extracellular Matrix of Fibrous Connective Tissues and Their Stability in Various Chemical Environments", J. Anat., 1998, vol. 192, pp. 391-405.
Sebag et al., "Morphology and ultrastructure of human vitreous fibers", Invest. Ophthalmol. Vis. Sci. 1989, vol. 30, pp. 1867-1871.
Sebag et al., "Pathogenesis of cystoid macular edema: An anatomic consideration of vitreoretinal adhesions", Survey Ophthalmol., 1984, vol. 28, pp. 493-498.
Sebag, "Age-related changes in human vitreous structure", Graefe's Arch Clin Exp Ophthalmol, 1987, vol. 225, pp. 89-83.
Sebag, "The Vitreous; Structure, Function, and Pathobiology" (1989), Chapter IV, Development and Aging of the Vitreous, pp. 73-95.
Shimada, H., et al., "Effects of an Anti-Prostaglandin Agent Added to the Irrigation Solution on Damage to the Anterior Segment in Monkey Eyes Induced by Pars Plana Vitrectomy", Database Biosis Online!, Biosciences Information Service, vol. 93, No. 8, 1989, pp. 823-829 (Abstract Only).
Supplemental European Search Report in Application No. EP 03709127.9 dated Mar. 8, 2005.
Supplementary European Search Report in Application No. EP 00916034.2 dated Oct. 20, 2004.
Supplementary European Search Report in Application No. EP 03709127.9 dated Jul. 11, 2005.
Supplementary European Search Report in Application No. EP 03709127.9 dated Jul. 5, 2005.
Supplementary European Search Report in Application No. EP 03711552.4 dated Apr. 11, 2005.
Supplementary Partial European Search Report in Application No. EP 00916034.2 dated Nov. 3, 2004.
Tartar et al., "A clinical study of the use of intravenous urea in glaucoma", American Journal of Ophthalmology; 52:323-331; 1961.
Wang et al., "Age-dependent Changes in the Basal Retinovitreous Adhesion", Invest. Ophthamol. Vis. Sci., 2003, vol. 44, No. 5, pp. 1793-1800.
Wolfer et al., "Diagnostic ophthalmology. Hypersensitive retinopathy." Can. Ve. J., vol. 38 (8) pp. 519-520, Aug. 1997.
Yarnell P.R., et al, "Plasma Urea kinetics in Urea infusion", Clinical Pharmacology and Toxicology. 1972;13: 558-562.
Yeo et al., "Extensions of Retinal Detachments as a Complication of Pneumatic Retinopexy", Arch. Ophthalmol, 1896, vol. 104, pp. 1161-1163.
Zadunaisaky JA et al., "Passage of sugars and urea across the isolated retinal pigment epithelium of the frog", Exp Eye Res 1976;23:191-6.
International Search Report for International Application No. PCT/US99/18237, mailed on Mar. 17, 2000.
Caliskan et al., "Intraoperative Mitomycin C for Pterygium Surgery," *Ophthalmology*, vol. 106(2), pp. 208-209 (Feb. 1999).
Ogura, "liposome used for an intraocular time-controlled delivery system," *Igaku-no-Ayumi* (*Progress in Medical Science*), published by Ishiyaku Publishers, Inc., Japan, vol. 162(3), p. 220 (1992).

\* cited by examiner

TREATMENT OF OPHTHALMIC DISORDERS USING UREA

CROSS-REFERENCE TO RELATED APPLICATIONS

This application is a continuation of U.S. application Ser. No. 11/585,400, filed Oct. 23, 2006, which is a division of U.S. application Ser. No. 10/367,614, filed Feb. 13, 2003, which claims the benefit of U.S. Provisional Application Ser. No. 60/357,347, filed Feb. 13, 2002, and U.S. Provisional Application Ser. No. 60/357,574, filed Feb. 15, 2002, and which is also a continuation-in-part application of U.S. application Ser. No. 10/215,680, filed Aug. 9, 2002, now U.S. Pat. No. 7,008,960, which is a continuation application of U.S. application Ser. No. 09/517,798, filed Mar. 2, 2000, now U.S. Pat. No. 6,462,071. The contents of all the foregoing patent applications are hereby incorporated by reference in their entireties.

FIELD OF THE INVENTION

This invention relates generally to the use of stabilized aqueous solutions of urea or urea derivatives for administration to the eyes of humans or other mammals. Urea and urea derivatives liquefy the vitreous humor and induce a posterior vitreous detachment thereby separating the cortical vitreous from the inner limiting lamina of the retina. The strong attachment of the cortical vitreous to the inner limiting lamina of the retina creates traction on the retina which results in rhegmatogenous retinal tears, idiopathic macular holes as well as cystoid macular edema. This separation of the cortical vitreous from the inner limiting lamina of the retina by urea or urea derivatives eliminates the vitreoretinal traction which allows the non surgical re-attachment of the retinal tear(s), the closure of the macular hole, and the resolution of cystoid macular edema.

BACKGROUND OF THE INVENTION

A. Anatomy of the Human Eye

In human beings, the anatomy of the eye includes a "vitreous body" which occupies approximately four fifths of the cavity of the eyeball, behind the lens. The vitreous body is formed of gelatinous material, known as the vitreous humor. Typically, the vitreous humor of a normal human eye contains approximately 99% water along with 1% macromolecules including: collagen, hyaluronic acid, soluble glycoproteins, sugars and other low molecular weight metabolites.

The retina is essentially a layer of nervous tissue formed on the inner posterior surface of the eyeball. The retina is surrounded by a layer of cells known as the choroid layer. The retina may be divided into a) an optic portion which participates in the visual mechanism, and b) a non-optic portion which does not participate in the visual mechanism. The optic portion of the retina contains the rods and cones, which are the effectual organs of vision. A number of arteries and veins enter the retina at its center, and splay outwardly to provide blood circulation to the retina.

The posterior portion of the vitreous body is in direct contact with the retina. Networks of fibrillar strands extend from the retina and permeate or insert into the vitreous body so as to attach the vitreous body to the retina. (Sebag, J. Graefe's Arch. Clin. Exp. Ophthalmol. 225, 89-93; 1987)

B. The Causes, Treatments and Clinical Sequelae of Rhegmatogenous Retinal Tears, Macular Holes and Cystoid Macular Edema Diabetic retinopathy, trauma, and other ophthalmological disorders sometimes result in rupture or leakage of retinal blood vessels with resultant bleeding into the vitreous humor of the eye (i.e., "intravitreal hemorrhage"). Such intravitreal hemorrhage typically manifests as clouding or opacification of the vitreous humor.

The human vitreous gel undergoes progressive liquefaction with age. After the age of 40 years, there is a steady increase in observed liquefied vitreous associated with a decrease in vitreous gel volume so that by the age 80 years more than half of the vitreous is liquefied (McLeod, D, et al. Trans. Ophthal. Soc. UK, 1997; 97:225-231). Light microscopic studies of whole human vitreous have demonstrated that vitreous liquefaction initially occurs in pockets, which then coalesce (Sebag. J, et al. Invest. Ophthalmol. Vis. Sci. 1989; 30: 1867-1871). These processes eventually result in rhegmatogenous posterior vitreous detachment (PVD). PVD is usually a sudden event during which liquefied vitreous from the center of the vitreous body bursts through a hole in the posterior vitreous cortex and then dissects the residual cortical gel away from the inner limiting lamina of the retina (Larsson, L. et al. Graefe's Arch. Clin. Exp. Opthalmol. 1985; 223: 92-95). The residual vitreous gel then collapses forward to occupy an anterior position in the vitreous cavity. This process may induce a tear in the retina which, in the presence of residual vitreoretinal traction around the break, can result in rhegmatogenous retinal detachment (McLeod, D. et al. Trans. Opthal. Soc. UK 1997; 97: 225-231). Vitreoretinal traction may also result in macular hole formation and it has been suggested that some forms of cystoid macular edema are due to vitreoretinal traction during incomplete PVD (Sebag, J. et al. Survey Opthalmol. 1984; 28: 493-498). In cases where the rhegmatogenous PVD is accompanied by a retinal tear or detachment, it is important that such retinal tear or detachment be promptly diagnosed and surgically repaired. Failure to promptly diagnose and repair the retinal tear or detachment may allow photoreceptor cells of the retina, in the region of the tear or detachment, to die. Such death of the photoreceptor cells of the retina may result in loss of vision. Furthermore, allowing the retinal detachment to remain unrepaired for such extended period of time may result in further intravitreal hemorrhage and/or the formation of fibrous tissue at the site of the hemorrhage. Such formation of fibrous tissue may result in the formation of an undesirable fibrous attachment between the vitreous body and the retina.

The typical surgical procedure used for repair of retinal tears or detachment requires that the surgeon be able to look through the vitreous humor, to visualize the damaged region of the retina (i.e., "transvitreous viewing of the retina"). When intravitreal hemorrhage has occurred, the presence of the hemorrhagic blood within the vitreous can cause the vitreous to become so cloudy that the surgeon is prevented from visualizing the retina through the vitreous. Such hemorrhagic clouding of the vitreous can take ~12 months or longer to clear sufficiently to permit trans-vitreal viewing of the retina.

The term Pneumatic Retinopexy was used by Hilton and Grizzard (Hilton, G. F. et al. Ophthalmology 1986; 93: 626-641) as a designation for a nonincisional retinal detachment operation consisting of an intravitreal injection of an expandable gas with cryotherapy and/or photocoagulation of the retinal break(s). Patient positioning oriented the gas bubble to close the retinal break(s), allowing spontaneous resorption of the subretinal fluid. Other authors have reported the complications of subretinal gas (McDonald, H. R. et al. Opthalmology, 1987; 94: 319-326), new retinal break formation (Poliner, L. S. et al. Ophthalmology, 1987; 94: 315-318), macular detachment (Yeo, J. H. et al. Arch. Opthalmol. 1986; 104:

1161-1163) and possible lower success rate in aphakic and pseudophakic eyes (Chen, J. C. et al. Ophthalmology, 1988; 95: 601-608).

Pneumatic Retinopexy is a method of retinal detachment repair which uses cryopexy or photocoagulation in combination with intravitreal gas injection to effect an internal tamponade of retinal breaks. Extension of existing retinal detachments with migration of subretinal fluid into the macula has been reported after pneumatic Retinopexy (Yeo, J. H. et al. Arch. Ophthalmol. 1986; 104: 1161-1163). The present report documents the occurrence of new retinal tears with associated retinal detachment in previously uninvolved quadrants in 20% of the patients within 2-4 weeks of pneumatic Retinopexy (Poliner, L. S. et al. Opthalmology, 1987; 94: 315-318). In these patients the original retinal detachments completely resolved. New retinal tears and associated detachments then developed opposite the original break with vitreous condensation and traction in previously uninvolved quadrants.

The majority of macular holes are "idiopathic" because they occur in eyes that have no previous ocular pathology. Macular holes can form immediately after blunt trauma. Besides trauma, other ocular problems have been associated with macular hole formation, including cystoid macular edema, epiretinal membranes, vitreomacular traction syndrome, rhegmatogenous retinal tears, hypertensive retinopathy, and proliferative diabetic retinopathy (Aaberg, T. M. Survey Opthalmol. 1970; 15: 139-162).

The hallmark complaint of idiopathic macular hole formation is painless central vision distortion or blur of acute or subacute nature. Central visual acuity is initially diminished only mildly; however, as the macular hole progresses over weeks to months, the visual acuity usually deteriorates, then stabilizes around the 20/200 to 20/800 level, and a macular hole diameter of 500 µm.

Examples of substances which have been purported to cause vitreal liquefaction and/or posterior vitreous detachment, or disinsertion are found in the U.S. Pat. Nos. 4,820,516 (Sawyer), 5,292,509 (Hageman), and 5,866,120 (Karageozian et al.).

There exists a need in the prior art for the elucidation and development of new materials and methods for accelerating the liquefaction of the vitreous and the induction of posterior vitreous detachment, or disinsertion of the vitreous.

C. Prior Therapeutic Applications of Urea and Urea Derivatives.

U.S. Pat. Nos. 5,470,881 (Charlton et al.), 5,629,344 (Charlton et al.) have described the topical application to the cornea or the "surface" of the eye of urea and/or urea derivatives to treat ocular conditions such as dryness, non-infectious keratitis, irregularities of the corneal or conjunctival epithelium, ocular scarring and "subjective irritations" of the eye. It is important to note that the urea formulations that have been described in the above mentioned patents utilize formulations which are non-aqueous in nature. These formulations contain hydrophobic non-aqueous systems like white petrolatum, mineral oil, and anhydrous liquid lanolin. Some of the formulations described are aqueous in nature; however, in place of urea the authors suggest the use of urea derivatives like ureidopropionic acid, or allantoin.

In the past, some aqueous urea preparations were reported to hydrolyze, thus producing ammonia as a byproduct. Ammonia is toxic to the eye when applied topically, and is even more toxic when applied intravitreally. Thus, Urea is a small molecule having a molecular weight of 60.06. Urea is somewhat basic, the pH of a 10% water solution is 7.2. Urea is very soluble in water, ethanol, methanol and glycerol; however, it is practically insoluble in chloroform or ether. Urea is colorless to white, prismatic crystals or white crystalline powder which stored under dry conditions is stable at room temperature. Aqueous urea solutions freshly prepared are clear, colorless and odorless. However, aqueous urea solutions gradually degrade and develop an odor of ammonia.

Urea is a product of the metabolism of proteins in the human body, it is excreted in human urine in average amounts of 30 gm/day. Urea has been widely used in medicine. Urea Solution for Injection has been an Official Monograph in the United States Pharmacopoeia/National Formulary (USP 24, 2000, pp. 1730), for over 40 years. Urea for injection (intravenous) had been a US Food and Drug approved product for over 20 years. The Urea product was registered and sold in the United States by Abbot Pharmaceutical Co. in 1961, under the trade name of Ureaphil. The Physicians' Desk Reference (PDR, Edition 1961, Medical Economics Publishing) lists the Urea for injection 1961 through 1979. References indicate that Urea for Injection was also registered and sold in numerous International countries as an osmotic diuretic for the reduction of intracranial pressure as well as for the reduction of intraocular pressure in subjects with Glaucoma. (Tartar, R. C. et al. American Journal of Opthalmology: 52:323-331; 1961). In addition, urea has been used intravenously to treat painful crisis of sickle-cell disease. (McCurdy, P. R. I.V. "Urea treatment of the painful crisis of Sickle Cell Disease" New England Journal of Medicine. 285: 992-994; 1971).

Urea has been used topically as a dermatological active ingredient in the treatment of Psoriasis, ichthyosis, atopic dermatitis and removal of excess keratin from dry skin. (Remington. "The Science and Practice of Pharmacy" 19 Edition, Chapter 62, pp. 1041-1042, 1995).

SUMMARY OF THE INVENTION

In accordance with the present invention, urea, a urea derivative, thiourea, a thiourea derivative, guanidine, a guanidine derivative or a compound having General Formula I (below) is administered intravitreally to liquefy the vitreous humor and induce a posterior vitreous detachment thereby facilitating separation of the cortical vitreous from the inner limiting lamina of the retina. The strong attachment of the cortical vitreous to the inner limiting lamina of the retina creates traction on the retina, which results in rhegmatogenous retinal tears, idiopathic macular holes as well as cystoid macular edema. This separation of the cortical vitreous from the inner limiting lamina of the retina by urea or urea derivatives eliminates the vitreoretinal traction which allows the non surgical re-attachment of the retinal tear(s), the closure of the macular hole, and the resolution of cystoid macular edema, among other things. In addition, the occurrence of new retinal tears with associated retinal detachment in pneumatic Retinopexy patients are completely eliminated. The compounds in addition to urea, thiourea, guanidine and derivatives thereof, other compounds useable to carry out the methods of the present invention have the General Formula I, as follows:

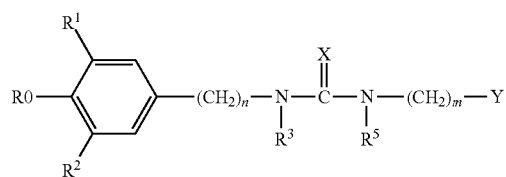

Wherein:

R is hydrogen, $C_1$-$C_8$ alkyl, $C_3$-$C_8$ cycloalkyl, $C_1$-$C_6$ alkylphenyl or hydroxyl protecting group;

$R^1$ and $R^2$ are each independently hydrogen, $C_1$-$C_6$ alkyl, $C_3$-$C_8$ cycloalkyl, $C_2$-$C_6$ alkynyl, $C_1$-$C_6$ alkoxy, $C_2$-$C_6$ alkenyl, $C_2$-$C_6$ alkenyl, —S(O)q($C_1$-$C_6$ alkenyl) or

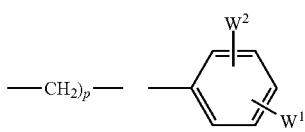

Wherein A is —CH$_2$—, —O—, —S—, —S(O)— or —S(O)$_2$—: W$^1$ and W$^2$ are each independently hydrogen, halo, hydroxyl, C$_1$-C$_4$ alkyl, C$_1$-C$_4$ alkoxy, C$_4$ alkylthio, C$_2$-C$_4$ alkenyl, or, C$_2$-C$_4$ alkynyl;

R$^3$ is hydrogen, C$_1$-C$_8$ alkyl, C$_8$ cycloalkyl, or, C$_1$-C$_6$ alkylphenyl;

X is O, S, or NR$_4$;

R$^4$ is hydrogen, C$_1$-C$_6$ alkyl, C$_1$-C$_4$ alkylphenyl or, C$_1$-C$_6$ alkoxy;

R$^5$ is hydrogen, C$_3$-C$_8$ cycloalkyl or C$_1$-C$_8$ alkyl;

Y is

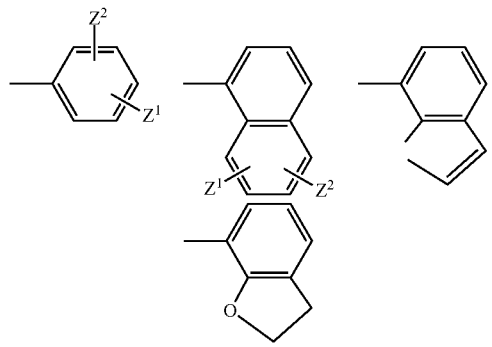

Wherein Z$^1$ and Z$^2$ are each independently hydrogen, C$_1$-C$_6$ alkyl, C$_3$-C$_8$ cycloalkyl, C$_1$-C$_6$ alkoxy, hydroxyl, C$_2$-C$_4$ alkenyl, C$_2$-C$_6$ alkyl, C$_1$-C$_6$alkylthio, halo, trifluoromethyl or —NR$^6$R$^7$;

R$^6$ and R$^7$ are each independently hydrogen, C$_3$-C$_8$ cycloalkyl, C$_1$-C$_6$ alkyl, C$_1$-C$_4$ alkylphenyl;

n is 1 to 6 all inclusive;

m and p are each independently 0 to 6, both inclusive;

q is 0, 1 or 2; and pharmaceutical salts thereof.

Further in accordance with the present invention, there are provided methods for treating various opthalmological disorders in human or veterinary patients by administering to the patient a therapeutically effective amount of urea, a urea derivative, thiourea, a thiourea derivative, guanidine, a guanidine derivative or a compound having General Formula I. The compound may be injected directly into the vitreous body of the eye (i.e., intravitreal injection) or may be administered by any other route that causes distribution of a therapeutically effective amount of the compound to the vitreous body. The compound may be administered for the purpose of treating specific ocular diseases or conditions associated with increased intraocular pressure and alterations of the vitreous humor. In one embodiment, the formulations induce a posterior vitreous detachment from the retina thereby separating the cortical vitreous from the inner limiting lamina of the retina. This separation of the cortical vitreous from the inner limiting lamina of the retina by urea or urea derivatives eliminates the vitreoretinal traction which allows the non surgical re-attachment of the retinal tear(s), the closure of the macular hole, and the resolution of cystoid macular edema, among other things. In addition, the occurrence of new retinal tears with associated retinal detachment in pneumatic Retinopexy patients are completely eliminated.

Still further in accordance with the present invention, there are provided methods for treating rubeosis and/or neovascular glaucoma. Rubeosis is a term that describes abnormal blood vessel growth on the iris and the structures in the front of the eye which are normally devoid of visible blood vessels. Typically, rubeosis results from retinal ischemia in patients who suffer from diabetic retinopathy or vein occlusion. Because the retina is deprived of normal blood flow, the body causes these abnormal blood vessels to form as a compensatory mechanism to supply oxygen to the eye. Unfortunately, the formation of these abnormal vessels often results in obstruction of the angle and/or trabecular meshwork through which aqueous fluid drains from the front of the eye. This causes an elevation in intraocular pressure or "neovascular glaucoma" and a resultant loss of peripheral vision. The present invention provides a treatment of rubeosis by administration to the vitreous body of the affected eye an amount of a) urea, a urea derivative, thiourea, a thiourea derivative, guanidine, a guanidine derivative or a compound having General Formula I, b) a nonsteroidal antiinflamatory agent (e.g., ketoralac, diclofenac, etc.) or c) the combination of i) urea, a urea derivative, thiourea, a thiourea derivative, guanidine, a guanidine derivative or a compound having General Formula I and ii) a nonsteroidal antiinflamatory agent (e.g., ketoralac, diclofenac, etc.) sufficient to lessen or prevent the neovascularization of the iris and/or other structures in the front of the eye.

Still further in accordance with the present invention, there are provided methods for protecting nerves from damage or for treating damaged nerves to cause regeneration and/or restoration of some impulse transmission through the nerve, by administering or contacting with the affected nerve a therapeutic amount of urea, a urea derivative, thiourea, a thiourea derivative, guanidine, a guanidine derivative or a compound having General Formula I. This method may be used to treat or prevent damage or diminished sensory and/or motor impulse transmission in any nerve, including optic nerves, central nerves (e.g., brain and spinal chord) and peripheral nerves. For this application the compound may be administered by any suitable route including intravitreal injection (to treat or prevent damage to the optic nerve), injection or delivery into the affected nerve, intrathecal, intracranial or intraventricular injection (to treat or prevent damage to central nerves of the brain or spinal chord) or injection or implantation next to or in proximity to the affected nerve.

Still further aspects and elements of the present invention will become apparent to those of skill in the art upon reading and understanding of the following detailed description and examples.

DETAILED DESCRIPTION

The preferred route of administration of the formulations and/or compositions disclosed herein is by intravitreal injection, whereby an aqueous solution of urea, thiourea, guanidine, a derivative of urea, thiourea or guanidine or a compound having General Formula I as shown above is injected directly into the vitreous body located within the posterior chamber of the eye. Alternatively, however, a vitreous liquefying and PVD inducing amount of such compound may be administered by any other suitable route of administration (e.g., topically, etc.) which results in sufficient distribution of the compound(s) to the vitreous body in sufficient amount to cause the desired vitreous liquefaction and posterior vitreous detachment effect.

The preferred injectable aqueous solution of stabilized urea may contain, certain inactive ingredients which cause the solution to be substantially hypotonic, isotonic, or hypertonic and of a pH range of 4.5-9.0 which is non toxic for injection into the eye. Such solution of stabilized urea for injection may be in glass vials or pre-filled syringes maintained at room temperature or refrigerated temperature, ready for use. In addition such solutions of stabilized urea may be initially lyophilized to a dry state and thereafter, may be reconstituted prior to use.

Urea employed in the invention method can be obtained 99.0-100.5% purity from several Manufacturers of fine chemicals.

The present invention provides stabilized aqueous urea solutions which comprise a) urea (or a urea derivative), b) sodium chloride, c) citric acid and d) water. One specific example of such a solution is shown in Table I, as follows:

TABLE I

Stabilized Urea Formulation

| Ingredient | Quantity |
| --- | --- |
| Urea | 0.01%-30.0% by weight |
| Citric Acid | 0.00001%-1.0% by weight |
| Sodium Chloride | 0.05%-3.6% by weight |
| Sterile water for Injection USP | Q.S 100% by weight |

In the stabilized aqueous urea solutions of the present invention, the urea concentration is typically in a range of about 0.003 mg per 50 μl to about 15 mg per 50 μl. In one embodiment, urea is provided in the formulation or composition in an amount between 0.005 mg per 50 μl to 7.5 mg per 50 μl. Citric acid is typically provided in a range between about 0.00001% to 1.0%, and in one embodiment, the citric acid is present in an amount between 0.00007% to 0.007%. Sodium chloride is typically provided in the formulation or composition in an amount between 0.05% to 3.6%, and in one embodiment, sodium chloride is provided in an amount between 0.9% and 1.8%. In a preferred embodiment, the composition comprises a combination of urea in an amount between about 0.005 mg per 50 μl to 7.5 mg per 50 μl, between 0.00007% and 0.007% citric acid, and between 0.9% to about 1.8% sodium chloride. The formulations disclosed herein may have a pH from about 4.0 to about 9.0, and in a preferred embodiment, the pH is less than 7.0, for example, in a range of 4.0 to 6.5. The formulations may also contain one or more buffers, such as, phosphate buffers, acetate, and/or glycine.

These formulation ingredients are typically initially dissolved in sterile water, sterile filtered and subsequently dispensed as a solution into glass or plastic vials or glass or plastic syringes. In addition the solution could be lyophilized to a dry composition. Thus, the pharmaceutical formulations are either liquid formulations, lyophilized formulations, and/or sterile powders. The formulations may be stored in pre-filled syringes, in glass vials, and may be stored at room temperature, refrigerated temperature, and frozen temperatures in a sealed condition with little degradation over prolonged periods of time, for example over one year, and in certain embodiments, over three years.

Tables II-IV below show specific examples of stabilized urea preparations that are within the general formulation set forth in the foregoing Table I.

TABLE II

| Ingredient | Quantity |
| --- | --- |
| Urea USP/NF | 1.50% |
| Citric Acid USP/NF | 0.0007% |
| Sodium Chloride USP/NF | 0.9% |
| Sterile Water for Inj. USP | Q.S 100% |

TABLE III

| Ingredient | Quantity |
| --- | --- |
| Urea USP/NF | 1.50% |
| Sodium Chloride USP/NF | 0.9% |
| Sterile Water for Inj. USP | Q.S 100% |

TABLE IV

| Ingredient | Quantity |
| --- | --- |
| Urea USP/NF | 1.50% |
| Sterile Water for Inj. USP | Q.S 100% |

As described in the following examples, the formulations of a stabilized aqueous solution of urea set forth in Table I, II, III and Table IV may be injected directly into the vitreous of the eye at dosage levels which bring about desirable therapeutic effects, including but not necessarily limited to the vitreous liquefaction and PVD induction effect of the present invention, without causing significant toxicity to the eye or associated anatomical structures. Among other things, and for example, the amount of urea present in the formulations may be provided in amounts to enhance the therapeutic effects mediated by one or more therapeutic agents. While not wishing to be bound by any particular theory or mechanism of action, it seems that a therapeutic agent that is co-administered with a formulation containing urea is more effectively distributed in the eye to provide a desired therapeutic effect. In other words, coadministration with urea advantageously seems to provide enhanced bioavailability of other therapeutic agents so that the other therapeutic agents can provide one or more therapeutic effects. As used herein, the term "coadministered" does not mean that the urea and the therapeutic agents must be administered precisely at the same time. Instead, in reference to the disclosure herein, coadministration refers to the administration of one or more therapeutic agents, other than urea, at a time in which the urea has provided a desired therapeutic effect. Thus, the one or more additional therapeutic agents may be administered in the same formulation comprising urea, or the therapeutic agents may be administered shortly before or after the administration of a formulation containing urea.

In addition, methods of treating neuropathies have also been invented by administering a formulation or composition containing an amount of urea effective to enhance neuronal activity, such as neurotransmission of one or more neurons. Administration of urea-containing formulations results in enhanced optic nerve function in patients who experienced reduced optic nerve function.

Example I

Treatment of Retinal Tears

Seven male and five female human patients having an average age of 47 years were observed to have single or multiple retinal tears, in addition 9 of the 12 patients had macular detachment. All patients received pneumatic Retinopexy treatment 3 days after intravitreal injection of 1.5 mg of urea in 50 µl of aqueous solution prepared according to the formulation set forth in Table 11 above. Ophthalmoscopic as well as biomicroscopic examination of all eyes showed no adverse effects of the intravitreal injection of the urea solution. Within 3-7 days after urea injection, 11/12 patients had developed PVD, only 1/12 patients had not developed PVD. Within 90 days of the urea injection that one patient also developed PVD.

Within 3 days of treatment 9/12 patients had complete retinal reattachment and macular attachment, and within 7 days all 12 patients had complete retinal reattachment and macular attachment. All patients were followed up for a period of 90 days, none of the patients experienced an occurrence of new retinal tears with associated retinal detachment.

It has been reported that, only 3% of patients treated by Retinopexy without prior urea treatment improved more than 2 lines of visual acuity (11 letters) at 1 month post Retinopexy and only 7% of the patients improved more than 2 lines of visual acuity (11 letters) at 6 months post Retinopexy. (Tornambe, P. E. et. al. Opthalmology, 1989; 96: 772-783). In this example, 64% of patients who received intravitreal urea injection 3 days prior to pneumatic Retinopexy exhibited an improvement of more than 2 lines of visual acuity (11 letters), and 64% of the patients showed an improvement of more than 2 lines of visual acuity (11 letters) at 6 months post Retinopexy. Also, at 1 month after Retinopexy, the urea-treated patients exhibited an average improvement in visual acuity of 3.9 lines on the eye chart (20 letters) and at 6 months after the Retinopexy, the average improvement of visual acuity per urea-treated patient was 4.2 lines (21 letters). Thus, it is concluded that a) the urea treatment facilitated re-attachment of the retinal tears as well as the reattachment of the detached macula of the patients after administration of formulations containing urea, b) as a result of the induction of PVD, the occurrence of new retinal tears with associated retinal detachment does not occur and c) there was improvement in vision in 64% of the Retinopexy patients who received urea treatment compared to only 3%-7% of Retinopexy patients who did not receive urea treatment.

Example II

Treatment of Idiopathic Macular Hole

A female patient 58 years old was observed to have a 450 µm idiopathic macular hole of 6 months duration. The macular defect was classified as a stage 3 macular hole, and the patient's visual acuity was recorded at 20/400 at a baseline time point prior to urea treatment. The subject was administered a single intravitreal injection of a formulation containing 1.5 mg of urea in a 50 µl solution prepared in accordance with the formulation of Table III above, and within 7 days the patient had a complete Posterior Vitreous Detachment (PVD). Ophthalmoscopic as well as Biomicroscopic examination of the patient's eye showed no adverse effects of the intravitreal injection of the urea solution. Seven days after the intravitreal urea injection the patient was administered an intravitreal injection of 0.3 ml of expandable gas ($C_3F_8$).

One week after administration of the gas, the size of the macular hole had decreased from 450 µm to a smaller size of 200 µm and the patient's vision had improved from a baseline visual acuity of 20/400 to 20/80. Two weeks post treatment the size of the macular hole had decreased from 450 µm to a smaller size of 90 µm and the patient's vision had improved from a baseline visual Acuity of 20/400 to 20/70. Four weeks post treatment the size of the macular hole had decreased from 450 µm to a smaller size of 60 µm and the patient's vision had improved from a baseline visual acuity of 20/400 to 20/60.

Stage 3 macular holes in patients who have not been administered the formulations disclosed herein do not close by themselves, the conventional way of treating macular holes is to perform a vitreous surgery. The surgery of macular holes has centered around three steps: a) the separation of the posterior hyaloid from the macula and the posterior pole of the eye; b) peeling of the perihole tissue; and c) use of long acting gas and face-down positioning. The risks of vitreous surgery and the mechanical membrane peeling of the posterior hyaloid by suction may be traumatic to the optic nerve head or the retina itself, leading to retinal hemorrhage, damage to the nerve fiber layer, or even perhaps retinal breaks leading to poor vision.

By administering the PVD-inducing amount of a compound of the present invention, the need for vitreous surgery may be completely eliminated. In this manner, the possible complications associated with vitreous surgery and resulting poor vision are avoided. As discussed herein, the compounds of this invention liquefy the vitreous humor and induce a posterior vitreous detachment thereby separating the cortical vitreous from the inner limiting lamina of the retina without the need for mechanical disruption of the vitreous. This separation of the cortical vitreous from the inner limiting lamina of the retina eliminates the vitreoretinal traction and thereby allows for non-surgical re-attachment of the retinal tear(s) and closure of the macular hole.

Example III

Intravitreal Urea Injection as an Adjuvant in Pneumatic Retinopexy

The present invention provides a method to reduce vitreoretinal traction and induce total posterior vitreous detachment (t-PVD) in subjects with primary regmatogen retinal detachment (PRRD) susceptible of treatment by pneumatic retinopexy was practiced by administering a formulation containing urea formulation set forth in Table II (VRT-1001) to the patients.

Consecutive patients of both genders with PRRD eligible for treatment with pneumatic retinopexy where enrolled after informed consent. A 0.3 ml intravitreal injection of the urea formulation set forth in Table II (VRT-1001, Vitreoretinal Technologies Inc., Irvine, Calif., USA) was administered, and pneumatic retinopexy was performed the next day, using 0.4 ml of 100% $C_3F_8$. Argon laser was applied as soon as possible to seal the retinal tears. Before, and 1, 7, 15, 30 and 90 days after the procedure, patients were monitored with biomicroscopy, posterior pole photography and retinal fluoroscein angiography (FAG), ultrasound (USG), and electroretinography (ERG). Visual capacity (VC), intraocular pressure (IOP), location of retinal lesions, vitreal status, retinal reapplication, complications, or adverse effects were all recorded. Complete and stable retinal application was considered as a success after a three month follow up.

Twelve eyes of 12 patients with PRRD were assessed. The ages of the patients ranged from between 27 and 60 years (mean 45.8±9.7). 58.3% did not have PVD and 41.7% had partial superior PVD by USG. After giving the VRT-1001 injection, all eyes presented t-PVD (75% collapsed and 25% without collapsed). A stable and complete retinal reapplication after the pneumatic retinopexy was achieved in all eyes during the follow up. Final VC was 20/40 or better, in 50% of the eyes (p<0.01). 8.3% maintained their initial VC. 8.3% had 1 line of improvement and 83.4% improved 2 lines. No change in intraocular pressure (IOP) was observed (mean 13.4±3 mmHg). The ERG was sub-normal, as expected after retinal detachments, with no evidence of retinal toxicity, showing an improvement at the end of the study. No alterations were observed in the FAG. Minor complications occurred and they were resolved within a few days. No adverse effects were reported.

The methods disclosed herein demonstrate that formulations containing urea are useful as an adjuvant in pneumatic retinopexy to improve the success rate in retinal reapplication.

Example IV

Treatment of Vitreous Hemorrhage

The formulations and treatments disclosed herein are also effective to treat vitreous hemorrhage. In this example, seven human patients were treated for diabetes-related nonclearing vitreous hemorrhage. Each patient received a single intravitreal injection of 100 μl of a formulation containing urea. The formulation used in this example contained 6% urea, 0.9% sodium chloride, and sterile water for injection (qs 100%).

All seven patients demonstrated clearance of their vitreous hemorrhage sufficient to treat the retina with photocoagulation within 2 to 4 weeks after injection. The rate at which the hemorrhagic blood cleared from the vitreous appears to have been significantly accelerated when compared with normal hemorrhage clearance rates seen in clinical practice.

Example V

Treatment as Adjunct to Vitrectomy

The treatment solutions disclosed herein may be injected intravitreally to cause pharmacologic vitreolysis alone or as an adjunct to a vitrectomy procedure.

In this example, five human patients requiring pars plana vitrectomy for various indications were treated one week prior to vitrectomy with a single intravitreal injection of 100 μl of a urea in aqueous solution. The formulation contained 6% urea, 0.9% sodium chloride, and sterile water for injection (qs 100%). All patients underwent routine vitrectomies 8 to 10 days after the urea injection. The minimum waiting time between the urea injection and the vitrectomy procedure is about 1 day to 3 days.

The patients who received the intravitreal injection of urea were noted to have complete vitreous liquefaction and collapse by one week after the injection (i.e., at the time of the virectomy procedure). Unlike patients who do not receive urea injection prior to vitrectomy, the vitreous of urea-treated patients in this example was liquefied to the extent that all or substantially all vitreous traction on the retina was relieved, thereby allowing the surgeon to remove the entire vitreous by aspiration with a syringe system. No vitrectomy cutter was used. Also, in this example, the administration of the urea-containing formulations resulted in a 70% decrease in surgical time relative to the procedures performed on patients who did not receive urea.

Example VI

Treatment of Diabetic Retinopathy

An association between a low incidence of progressive retinopathy in subjects with vitreous liquefaction and total PVD (either spontaneous or surgically induced), and a significant risk of aggressive proliferation of new blood vessels in patients with only a partial PVD has been well documented, both in diabetics, (Tagawa, H. et. al. Opthalmology, 1986; 93: 596-601 also Tagawa, H. et. al. Opthalmology, 1986; 93: 1188-1192) as well as in patients with central (Hikichi, T. et. al. RETINA, 1995; 15: 29-33) or branch vein occlusion (Kado, M. et. al. Am J. of Opthalmology, 1988; 105: 20-24). Histopathological observations suggest that the cortical vitreous can provide a scaffold for retinal neovascularization in diabetic retinopathy and other retino-vascular proliferative disorders.

Therefore the ability to prophylactically liquefy the vitreous, collapse the scaffold and induce PVD, could provide an important strategy for diabetic patients in the pre-proliferative phase to protect them against future retinal or optic disc neovascularization.

Injection of urea into the vitreous results in the breakdown of hyaluronic acid of the vitreous and liquefaction of the vitreous body within several days. In addition, disinsertion of the posterior vitreous has been observed in patients by the use of slit lamp biomicroscopy and in rabbits by specialized histological techniques after urea treatment.

A method of treating and/or preventing diabetic retinopathy includes a step of administering a formulation or composition containing urea to a patient.

Sixty-nine patients with nonproliferative diabetic retinopathy were each administered a single intravitreal injection of 50 μl of a urea formulation containing 3% urea, 0.9% sodium chloride, and sterile water for injection.

All 69 patients exhibited complete vitreous liquefaction and collapse within 2-4 weeks after administration of the formulation. The vitreous liquefaction and vitreous collapse in nonproliferative diabetic retinopathy patients would inhibit the growth and proliferation of the blood vessels, and thus inhibit the progression of diabetic retinopathy. All 69 (of the) patients were followed for six months following the procedure.

Example VII

Treatment of Retinitis Pigmentosa

In accordance with the present invention, urea, thiourea, guanidine and possibly the other compounds of General Formula I above may provide neuroprotective/neuroregenerative effects. In this particular example, patients suffering from retinitis pigmentosa were used to demonstrate the neuroprotective effects.

A double masked placebo controlled, randomized, dose escalation study was done in 32 human patients with retinitis pigmentosa. All patients were treated with a single intravitreal injection of 50 μl of a urea-containing formulation. Three groups of patients received different concentrations of urea. One group received a formulation containing 1.5% urea, 0.9% sodium chloride, and sterile water for injection. A second group received an identical formulation except the formulation contained 3.0% urea. A third group received an identical formulation except the formulation contained 6.0% urea. A placebo group received 50 μl of 0.9% sodium chloride.

Forty-seven percent of the patient reported an increase of at least 3 lines of best corrected visual acuity measured by ETDRS charts, whereas, only 14% of the placebo patients reported an increase of at least 3 lines of best corrected visual acuity measured by ETDRS charts.

The improvement demonstrated by the urea-treated patients corresponds to an average of 10 degrees of improvement in the patient's visual field. In this masked, placebo control study the neuroprotective/neuroregenerative effects of the urea formulation was demonstrated by a) the increase of visual acuity in 47% of the treated patients b) the corresponding enlargement or increase in the visual fields of these same patients. There was no dramatic increase in the visual field of the placebo control patients.

Example VIII

Treatment of Neuropathies

In accordance with the present invention, urea, thiourea, guanidine and possibly the other compounds of General Formula I above are effective to treat neuropathies (e.g., disorders or damage to nerves). In this example, 33 non sighted patients with optic nerve damage caused by trauma and/or glaucoma, with visual acuity of light perception or no light perception were administered a urea-containing formulation, as disclosed herein. The study was a double masked placebo controlled, randomized, dose escalation study conducted with 33 human patients with optic nerve damage. Patients were randomized into 5 groups, Group 1 of 5 patients, Group 2 of 4 patients, Group 3 of 8 patients, Group 4 of 8 patients and Group 5 of 8 patients. Each patient received a single intravitreal injection of 50 µl of an aqueous treatment solution, as follows:

| | |
|---|---|
| Group 1 | 0.9% sodium chloride (control) |
| Group 2 | 0.2% by weight Urea |
| Group 3 | 1.5% by weight urea |
| Group 4 | 3.0% by weight Urea |
| Group 5 | 6.0% by weight Urea |

Forty-three percent of the patients exhibited an increase of best corrected visual acuity measured by ETDRS charts. In Six patients the vision improved from No light perception to light perception, in 2 patients the vision improved from light perception to count fingers at 12 inches, in 2 patients the vision improved from no light perception to 20/400 and 20/800 vision and in 2 patients the vision improved from light perception to 20/600 and 20/800 vision. No patients in the placebo group reported any improvement in best corrected visual acuity as measured by ETDRS charts.

In another study, three patients with long standing (6 months or longer) optic nerve damage related to optic nerve tumors were treated with a single intravitreal injection of 100 µl of a 6% urea containing formulation. All three patient treated reported a significant improvement in visual acuity after treatment. The patients' visual acuity improved from an average of Count Fingers at 12 inches to 20/200.

Example IX

Treatment of Rubeosis

In accordance with the present invention, urea, thiourea, guanidine and possibly the other compounds of General Formula I alone and/or in combination with nonsteroidal antiinflamatory agents (e.g., ketoralac, diclofenac, flourbiprofen, Ibuprofen etc.) may be effective in treating rubeosis. In this example, a single patient suffering from rubeosis received a single intravitreal injection of 100 µl of an aqueous solution containing 6.0% by weight urea, 0.9% by weight sodium chloride, and 0.2% by weight ketoralac in a (and) sterile water for injection (qs 100%). The patient was followed for 10 weeks.

The patient was noted to have a dramatic reduction in neovascularization of the iris as documented by iris fluorescein angiography before and after the urea/keterolac injection.

Example X

Treatment of Diabetic Macular Edema

In accordance with the present invention, urea, thiourea, guanidine and possibly the other compounds of General Formula I above may be administered alone and/or in combination with a nonsteroidal antiinflamatory agent (e.g., ketoralac, diclofenac, flourbiprofen, ibuprofen, etc.) to treat macular edema. In this example, a patient with macular edema related to diabetic retinopathy received a single intravitreal injection of 100 µl of an aqueous solution containing 6.0% by weight urea, 0.9% by weight sodium chloride and 0.07% by weight ketoralac in sterile water for injection (qs 100%). The patient was noted to have a dramatic improvement in best corrected visual acuity of at least 3 lines by ETDRS measurements during the course of the 8 week monitoring cycle.

It will be understood by those of ordinary skill in the art, that the present invention is not limited to the specific examples and embodiments described here above. Rather, the present invention can be practiced using a wide equivalent variation of conditions, formulations and other parameters, without affecting the scope of the invention or any embodiment therein.

Also, all publications cited in this patent application are expressly incorporated by reference herein in their entirety.

What is claimed is:

1. A pharmaceutical composition for injection into a vitreous body of an eye, comprising a sterile aqueous solution, comprising:
   a) 3-30.0% urea by weight;
   b) 0.00001-1.0% citric acid by weight;
   c) 0.05-3.6% sodium chloride by weight; and
   d) sterile water for injection, Q.S. 100% by weight;
   wherein said pharmaceutical composition is stable and non-toxic when injected into the eye.

2. The pharmaceutical composition of claim 1, wherein the aqueous solution comprises 6.0-30.0% urea by weight.

3. The pharmaceutical composition of claim 1, wherein the aqueous solution comprises 15-30.0% urea by weight.

4. The pharmaceutical composition of claim 1, wherein the aqueous solution comprises urea in a concentration of about 7.5 mg urea per 50 µl.

5. The pharmaceutical composition of claim 1, wherein the aqueous solution comprises 0.00007-0.007% citric acid by weight.

6. The pharmaceutical composition of claim 1, wherein the aqueous solution comprises about 0.007% citric acid by weight.

7. The pharmaceutical composition of claim 1, wherein the aqueous solution comprises 0.9-1.8% sodium chloride by weight.

8. The pharmaceutical composition of claim 1, wherein the aqueous solution comprises about 0.9% sodium chloride by weight.

9. The pharmaceutical composition of claim 1, wherein the aqueous solution has a pH from about 4.0 to about 9.0.

10. The pharmaceutical composition of claim 1, wherein the aqueous solution has a pH from about 4.0 to about 6.5.

11. The pharmaceutical composition of claim 1, wherein the pharmaceutical composition is stable when stored at room temperature for at least about one year.

12. A dry pharmaceutical composition, obtainable by lyophilization of the sterile aqueous solution of claim 1.

13. A dry pharmaceutical composition, comprising urea, citric acid and sodium chloride, wherein each of the urea, citric acid and sodium chloride are present in the dry pharmaceutical composition in an amount sufficient to yield an aqueous solution upon reconstitution with water, the aqueous solution comprising:
   a) 3-30.0% urea by weight;
   b) 0.00001-1.0% citric acid by weight;
   c) 0.05-3.6% sodium chloride by weight; and
   d) water, Q.S. 100% by weight; and
   wherein after reconstitution of the dry pharmaceutical composition, the aqueous solution is non-toxic when injected into a vitreous body of an eye.

14. The dry pharmaceutical composition of claim 13, wherein upon reconstitution with water, the aqueous solution comprises a urea concentration of 6.0-30.0% by weight.

15. The dry pharmaceutical composition of claim 13, wherein upon reconstitution with water, the aqueous solution comprises a urea concentration of 15-30.0% by weight.

16. The dry pharmaceutical composition of claim 13, wherein upon reconstitution with water, the aqueous solution comprises a citric acid concentration of 0.00007-0.007% by weight.

17. The dry pharmaceutical composition of claim 13, wherein upon reconstitution with water, the aqueous solution comprises a citric acid concentration of about 0.007% by weight.

18. The dry pharmaceutical composition of claim 13, wherein upon reconstitution with water, the aqueous solution comprises a sodium chloride concentration of 0.9-1.8% by weight.

19. The dry pharmaceutical composition of claim 13, wherein upon reconstitution with water, the aqueous solution comprises a sodium chloride concentration of about 0.9% by weight.

20. The dry pharmaceutical composition of claim 13, wherein upon reconstitution with water, the aqueous solution has a pH from about 4.0 to about 9.0.

21. The dry pharmaceutical composition as claimed in claim 13, wherein upon reconstitution with water, the aqueous solution has a pH from about 4.0 to about 6.5.

22. The dry pharmaceutical composition of claim 13, wherein the dry composition is stable for at least one year at room temperature.

23. A dry composition comprising:
   a) 9-90 mg urea;
   b) 0.00003-3 mg citric acid; and
   c) 0.15-10.8 mg sodium chloride;
   wherein said dry composition is suitable for reconstitution with sterile water for injection to yield an aqueous solution comprising 3-30.0% urea and wherein the aqueous solution is non-toxic when injected into a vitreous body of an eye.

24. The dry composition of claim 23, wherein the composition comprises 18-90 mg urea.

25. The dry composition of claim 23, wherein the composition comprises 45-90 mg urea.

26. The dry composition of claim 23, wherein the composition comprises 0.00021-0.021 mg citric acid.

27. The dry composition of claim 23, wherein the composition comprises 0.021 mg citric acid.

28. The dry composition of claim 23, wherein the composition comprises 2.7-5.4 mg sodium chloride.

29. The dry composition of claim 23, wherein the composition comprises 2.7 mg sodium chloride.

30. The dry composition of claim 23, wherein the composition is stable when stored at room temperature for one year.

31. A kit for the preparation of an aqueous solution comprising urea, the aqueous solution being suitable for injection into a vitreous body of an eye, the kit comprising:
   a) a first container containing a dry composition comprising:
      i) 9-90 mg urea;
      ii) 0.00003-3 mg citric acid; and
      iii) 0.15-10.8 mg sodium chloride; and
   b) a second container containing at least 300 µL sterile water for injection.

32. The kit of claim 31, further comprising a syringe for intravitreal injection.

33. The kit of claim 31, wherein the dry composition comprises 45-90 mg urea.

34. The kit of claim 31, wherein the dry composition comprises 0.021 mg citric acid.

35. The kit of claim 31, wherein the first and second containers are glass vials.

36. The kit of claim 31, further comprising instructions for reconstitution and intravitreal injection.

* * * * *